(12) United States Patent
Grey

(10) Patent No.: US 8,126,542 B2
(45) Date of Patent: Feb. 28, 2012

(54) METHODS FOR PERFORMING PHYSIOLOGICAL STRESS TESTS

(75) Inventor: Alexander B. Grey, Sacramento, CA (US)

(73) Assignee: Somaxis, Inc., San Jose, CA (US)

( * ) Notice: Subject to any disclaimer, the term of this patent is extended or adjusted under 35 U.S.C. 154(b) by 191 days.

(21) Appl. No.: 12/332,111

(22) Filed: Dec. 10, 2008

(65) Prior Publication Data
US 2010/0145219 A1 Jun. 10, 2010

(51) Int. Cl.
*A61B 5/04* (2006.01)

(52) U.S. Cl. ...................................... 600/546

(58) Field of Classification Search .................. 600/546, 600/547, 300, 409, 544, 545, 587, 591, 595, 600/554; 128/898, 905; 340/825.19; 341/21; 345/157; 463/36; 607/45; 424/736; 514/530, 514/546, 457, 693, 543, 675
See application file for complete search history.

(56) References Cited

U.S. PATENT DOCUMENTS

| | | | |
|---|---|---|---|
| 4,291,705 A | 9/1981 | Severinghaus et al. | |
| 5,269,302 A | 12/1993 | Swartz et al. | |
| 5,474,082 A | 12/1995 | Junker | |
| 5,513,651 A | 5/1996 | Cusimano et al. | |
| 5,755,675 A | 5/1998 | Sihvonen | |
| 5,776,073 A | 7/1998 | Garfield et al. | |
| 5,964,719 A | 10/1999 | Costello et al. | |
| 6,453,194 B1 | 9/2002 | Hill | |
| 6,647,288 B2 | 11/2003 | Madill et al. | |
| 6,678,549 B2 | 1/2004 | Cusimano et al. | |
| 7,234,469 B2 | 6/2007 | Hanin | |
| 7,593,769 B1 * | 9/2009 | Ettare ........................... | 600/547 |
| 2001/0049471 A1 | 12/2001 | Suzuki et al. | |
| 2006/0240131 A1* | 10/2006 | Warrenburg et al. ......... | 424/736 |

FOREIGN PATENT DOCUMENTS

| | | |
|---|---|---|
| EP | 0880936 A2 | 12/1998 |
| JP | 10-305016 A | 11/1998 |

OTHER PUBLICATIONS

International Search Report and Written Opinion, mailed Jul. 1, 2010, as issued in connection with corresponding Patent Application No. PCT/US2009/067557, filed on Dec. 10, 2009.

* cited by examiner

*Primary Examiner* — Brian Szmal
(74) *Attorney, Agent, or Firm* — Machoff Golmore & Israelsen

(57) ABSTRACT

Systems and methods are provided for evaluating the risk of stress-related injury associated with a predetermined activity. One embodiment involves collecting physiological data while a subject performs a predetermined task, collecting psychological data while the subject performs a cognitive task, and ascertaining the risk of stress-related injury based on both the collected physiological data and the collected psychological data. Another embodiment involves presenting a subject with a plurality of mental and physical tasks during which physiological data, psychological data, and/or both is collected, and determining the risk of stress-related injury based on the data collected. Yet another embodiment includes a test circuit for measuring stress responses that includes both physiological test stations and psychological test stations. Physiological stress is evaluated in the form of surface electromyography data that is quantified into a single index value, as will be described in detail herein.

16 Claims, 8 Drawing Sheets

METHODS FOR PERFORMING PHYSIOLOGICAL STRESS TESTS

BACKGROUND OF THE INVENTION

Recent studies have indicated that many different types of stress contribute to many serious health problems. For example, physiological stress associated with some work-related and recreational activities can lead to stress-related injuries including repetitive strain injuries and cumulative trauma disorders, which are injuries of the musculoskeletal and nervous systems that may be caused by repetitive tasks, forceful exertions, vibrations, mechanical compression, or sustained positions. These painful and sometimes crippling disorders may develop gradually over periods of weeks, months, or years and include epicondylitis, tendinitis, low back disorders, cervical radiculopathy, ulnar nerve entrapment, carpal tunnel syndrome, and the like.

Also, the psychological stress associated with some work-related and recreational activities oftentimes also leads to health problems. Since its first description by Hans Selye in 1936, stress has been the subject of increasing number of scientific studies, and it is well established that stress is a factor both in the pathogenesis and the exacerbations of many diseases from the common cold to severe cardiovascular disorders.

In order to understand the high prevalence of medical disorders associated with stress, it is important to explore the manner in which physiological and psychological stressors affect muscle physiology and the physiology of muscle use over time. It is also important to be able to effectively compare muscle behavior and muscle use of individuals being assessed within a population by means of a standardized testing platform which reflects the various contributing factors to neuromuscular or musculoskeletal pathology. However, there has yet to be a standardized protocol for studying this relationship.

The subject matter claimed herein is not limited to embodiments that solve any particular disadvantages or that operate only in particular environments such as those described herein. Rather, such environments and disadvantages are provided only to illustrate examples of technology areas in which several embodiments may be practiced.

BRIEF SUMMARY OF THE INVENTION

Systems and methods are provided for evaluating the risk of stress-related injury associated with a predetermined activity. A method for accessing the physiological effect of physiological and psychological stressors on a subject is disclosed. The method includes presenting the subject with a first physiological stressor and receiving surface electromyography (sEMG) data points describing muscular activity of the subject while the subject is experiencing the physiological stressor. The method further includes presenting the subject with a first psychological stressor and receiving sEMG data points describing muscular activity of the subject while the subject is experiencing the psychological stressor. The method further includes accessing the physiological effect of the psychological and physiological stressors by analyzing the sEMG data points received.

A method for determining the risk of stress-related injury associated with a predetermined activity is disclosed. The method includes presenting a subject with a test circuit, the test circuit including a plurality of test stations, wherein each test station includes one or more physiological and/or psychological stressors. The method further includes collecting sEMG data points describing muscular activity of the subject while the subject is at a first test station experiencing a first physiological stressor. The method further includes calculating a first index value summarizing the sEMG data points collected while the subject is experiencing the first physiological stressor at the first test station. The method further includes collecting sEMG data points describing muscular activity of the subject while the subject is at a second test station experiencing a first psychological stressor. The method further includes calculating a second index value summarizing the sEMG data points collected while the subject is experiencing the first psychological stressor at the second test station. The method further includes determining the risk of stress-related injury associated with the predetermined activity based on the first and second index values.

A test circuit for accessing the physiological effect of mental and physical stressors on a subject is disclosed. The test circuit includes a first test station and a second test station. The first test station includes a first plurality of sEMG sensors for collecting first sEMG data describing muscular activity of the subject while the subject is experiencing a physiological stressor. The first test station further includes a first processing circuit communicably coupled to the first plurality of sEMG sensors for calculating a first index value based on the first sEMG data. The second test station includes a second plurality of sEMG sensors for collecting sEMG data describing muscular activity of the subject while the subject is experiencing a psychological stressor. The second test station further includes a second processing circuit communicably coupled to the second plurality of sEMG sensors for calculating a second index value based on the second sEMG data.

These and other features of the present invention will become more fully apparent from the following description and appended claims, or may be learned by the practice of the invention as set forth hereinafter.

BRIEF DESCRIPTION OF THE DRAWINGS

To further clarify the features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF SEVERAL EMBODIMENTS

Stress-related injuries and disorders oftentimes have both psychological and physiological components. It is well-known that mental stress may induce muscle tension and has been proposed to contribute to the development of several musculoskeletal disorders. Prolonged physical activity may lead to repetitive strain injuries and/or cumulative stress disorders. Principles of the present invention allow both the psychological components and the physiological components of stress to be evaluated and quantified. By exploring both physical and psychological stressors that induce neuromuscular stress responses, a better understanding of stress-related injuries may be achieved.

Systems and methods are provided for evaluating the risk of stress-related injury associated with a predetermined activity. One embodiment involves collecting physiological data while a subject performs a predetermined physical task, collecting physiological data while the subject performs a predetermined cognitive task, and ascertaining the risk of stress-related injury based on the collected physiological data.

Another embodiment involves presenting a subject with a plurality of mental and physical tasks during which physiological data is collected in the form of surface electromyography (sEMG) data. This embodiment involves analyzing the sEMG data and determining the risk of stress-related injury based on the sEMG data collected.

1. Measuring and Quantifying the Stress Response

According to the embodiments disclosed herein, physiological and psychological stress responses are evaluated as muscle activity as measured by sEMG. In sEMG, electrodes are attached to the surface of the skin overlying a muscle to measure the amount of electricity the muscle produces as muscle fibers contract. An sEMG signal is an electrical manifestation of the neuromuscular activation associated with a contracting muscle. The signal represents current generated by the ionic flow across the muscle fiber membrane which propagates through intervening tissues to reach the detection surface of the electrode. Thus, muscle activity can be objectified, quantified, and documented while a subject performs predetermined physical and psychological tasks in a test circuit.

Figure 1:
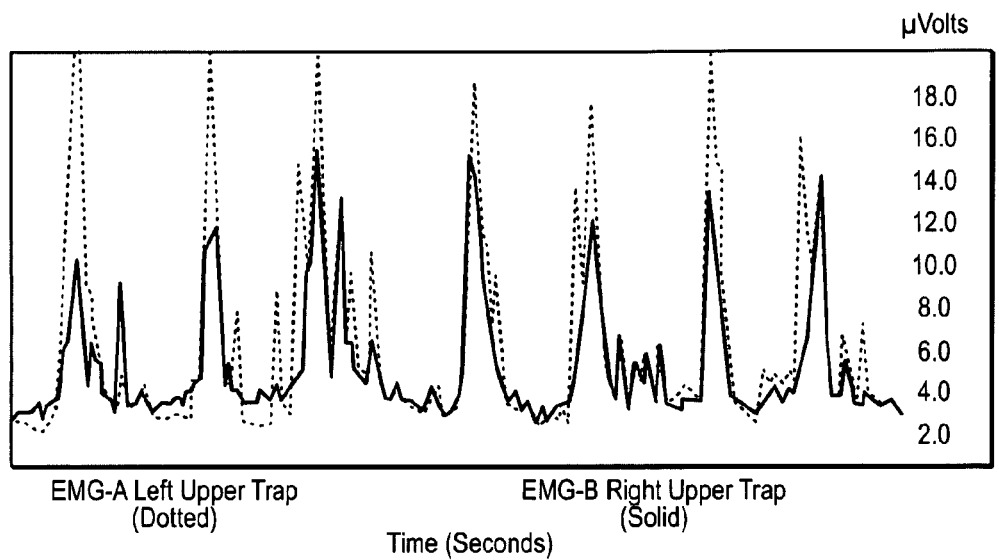
FIG. 1 illustrates an example display of sEMG values over time.

Typically, a healthy muscle in a resting state will show sEMG values around 2 microvolts, for example. During use, the muscle's activity level will spike upward, with values that depend greatly on the muscle in question, the neuromuscular/musculoskeletal health of the individual, and the kind of activity. For example, right and left upper trapezius activity while alternating sitting or standing (body position presumed to be the only variable) may look something like that shown in FIG. 1. The example shown in FIG. 1 illustrates that sEMG values can range from around 5 to 14 microvolts in such an example. During intense use, values may shoot up significantly higher, however, possibly even one or two orders of magnitude higher (e.g. 100-1000 microvolt range or more).

In one embodiment, the physiological stress response as measured in terms of sEMG data may be quantified in a single index value. The index is used to more concisely describe muscle activity over time. Put another way, an index describes muscle loading, implicit in which is the assumption of a timeframe. The index summarizes sEMG information that is comprised of a series of data points. These data points are typically represented in the format (X,Y) (e.g. see FIG. 1). The X axis refers to the point in time in which the value was taken, and the Y axis refers to the potential difference of the muscle at that point in time. For example, raw data can be processed according to many different algorithms, yielding a single value. This value, such as a raw number, can then be scaled. For example, the value can be scaled onto a 1-10 range, a 1-100 range, a color scale, a sound scale, or other methods with which to communicate, further process, and/or store the information.

sEMG data is bulky in the sense that thousands, tens of thousands, hundreds of thousands of data points, or more, can comprise a single graph. It is frequently up to the subjective opinion of the observer to assess the state of the muscle based upon the graph. However, according to the teachings herein, algorithms can be used to introduce objectivity into sEMG graph interpretation. There are different methods of arriving at this index value, which may represent different theories as to the significance of different aspects of an sEMG graph. Embodiments of methods for calculating index values from sEMG data points are also described in more detail in co-pending patent application Ser. No. 11/741,742, entitled "Surface Electromyography Index", filed Apr. 28, 2007, the contents of which are hereby incorporated by reference herein.

sEMG data can be collected using many different systems and apparatuses. For example, referring to FIG. 2, a system for collecting sEMG data is illustrated. The system includes sEMG conductive sensors 200 coupled to various muscles of an individual 205 under test. The sEMG conductive sensors 200 are coupled via wires 210, a wireless connection 220, or directly connected to a processing device, such as a conventional or special purpose computer 225. The computer 225 includes software and hardware for collecting the sEMG data which may be displayed by the computer 225. The computer 225 further includes software and hardware configured to analyze the sEMG data to calculate index value(s) and perform analysis according to the methods disclosed herein. The system illustrated in FIG. 2 can be combined with other apparatuses, such as motion detection, electrocardiography (EKG), electroencephalography (EEG) devices, and other systems as described in further detail hereinafter.

A. Examples of Methods of Index Calculation

Many different methods and algorithms can be used to quantify sEMG graphs into one or more index values. For example, the index calculation can include consideration of an area under a curve. Under this method, an integral of at least a portion of an sEMG graph can be taken or approximated. This approximation can either be standardized with respect to a consistent length of time, for example two minutes of activity, or described in terms of a unit time.

A weighted integral/double integral can also be considered. For example, the area under the weighted integral/double integral curve can be measured under the assumption that the data is most significant when closest to the bottom of the graph. To calculate this, a significance gradient is used such that 0 microvolts represents 100% significance, and 100 microvolts (arbitrary value for example only) represents 0% significance. The significance gradient may increase linearly or non linearly (or a combination thereof). The area under the curve is calculated taking this significance into account. This effectively minimizes the importance of spikes in the graph and emphasizes the troughs.

According to another embodiment, an area over a curve can be used to quantify sEMG graphs. The area over the curve is calculated or estimated by establishing a horizontal line parallel to the x-axis, the height of which is arbitrary—for example determined by the maximum height of the graph, or some distance from it. This area over the curve can be used to numerically represent the results of an sEMG graph. This method also emphasizes the troughs and deemphasizes the spikes in an sEMG graph that may be present.

According to another embodiment, any combination of high data points, low data points, and/or average data points can be used to quantify sEMG graphs. Also, other forms of indirect data may be used, such as derivatives (first, second, etc) of curves approximating at least a portion of an sEMG graph. This embodiment represents a number of different methods that may be varied in terms of the weights, or relative importance, associated with them. High points, low points, and averages of data points are significant values that can be used to calculate index variants. A high point (H), or point of inflection in which the first-order derivative changes from positive to negative, represents the height of a spike. A low point (L), or point of inflection in which the derivative changes from negative to positive, represents the depth of a trough. An average (A) is a mean for a given time interval. It is important to note that during calculation of high points and low points, a time interval or sensitivity range should be specified. The broader the range, the greater the amount of data is summarized by the index. The smaller the time-interval becomes, the more the index begins to approach an instantaneous rate of muscle loading. There are advantages and disadvantages to each range implementation.

In this method, for each time interval, the high points, low points, and average are calculated. If there are multiple high points and/or multiple low points, the average (or other distribution) of the high points and low points can be calculated and used in the following equation.

$$DH+CL+BA=E$$

, where E is the index, or sEMG index

The constants, D, C, and B, in the above equation represent the weight, or significance, of the high points, low points, and average, respectively. An example version of this equation is:

$$0.3H+0.6L+0.1A=E$$

This example places 60% significance on the low points, 30% significance on the high points, and 10% significance on the average. Any number of weights can be placed on the different constants D, C, and B in the above equation and any combination of high data points, low data points, average data points, and other direct or indirect data derived from sEMG data can be used, or excluded, from the calculation.

Other algorithms for calculating index values can also include other quantifiable derivations of an area under a curve, an area over a curve, high data points, low data points, and an average of data points. For examples, a ratio of high data points, low data points, and averages of data points can be used to calculate index values. Other forms of direct or indirect data based on the sEMG data can also be calculated. Thus, many different algorithms may be implemented to derive index values for sEMG data.

B. Processing Multiple Index Values

The index can be calculated for multiple segments. For example, if an individual is being tested over a two-minute time frame, in which there are four 30 second subdivisions which represent four different tasks, the index for each task can be calculated. The overall index for the complete test can be a simple average, or, if the significance of one task is greater than another, they could be weighted unevenly.

Weighting of the different parameters can be used for multiple muscle groups. For example, if sixteen muscles are being monitored, the index can be calculated for each group for a given period of time. These data points for the different muscle groups can then all be averaged together, or, if one muscle group has more significance than another, a weighted average can be calculated. This is useful when trying to determine the likelihood of different events. For example, testing for work-related upper-extremity disorders, specifically some forms of keyboard-induced repetitive strain injuries, may emphasize testing for overuse of muscles in the wrists and forearms and deemphasize muscles in the lower back.

C. Examples of the Significance and Uses of the Index

The index can be used to predict an individual's likelihood of developing repetitive strain injuries and related neuromuscular or musculoskeletal injuries that may result in chronic pain, as well as other unrelated conditions and/or symptoms. As shown in several studies, chronic overuse of muscles inflames tissue around muscle spindles creating trigger points. The tissue inflammation affects muscle spindles, inducing pain via interaction with innervated receptors within the spindle. This is thought to be a physiological basis for chronic pain. Therefore, a method of quantifying muscle activity can identify muscles operating above safe levels.

Figure 3:
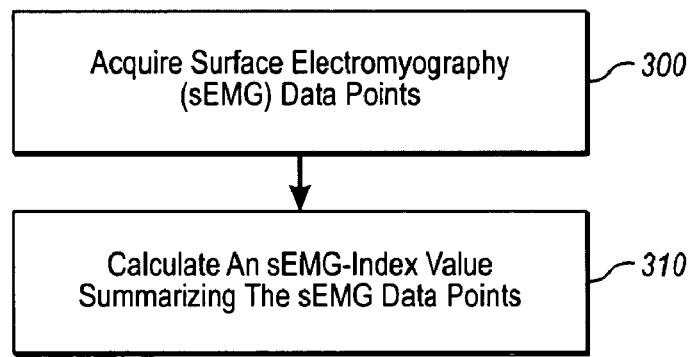
FIG. 3 illustrates a method for predicting an individual's likelihood of developing a medical condition, such as repetitive strain and related injuries.

For example, referring to FIG. 3, a method for predicting an individual's likelihood of developing a medical condition, for example one resulting in chronic pain, is illustrated. sEMG data points are acquired describing muscular activity of the individual (300). The data points can be acquired by placing at least two conductive sensors on the individual's skin some distance apart from one another at a particular location (or multiple locations). The potential difference (voltage) between each pair of points is measured as a single data point and multiple data points are measured over a period of time. The data points can be measured during rest (e.g., while the individual is sitting or lying down) and/or while the individual is performing various tasks. The data points can be stored in computer readable memory and accessed from the computer readable memory for processing and/or display.

An index is calculated from the sEMG data points acquired, where the index summarizes the sEMG data points acquired (310). The index can be calculated based on an area under a curve, wherein the curve approximates at least a portion of the sEMG data points. The index can also be calculated based on an area over the curve approximating the sEMG data points. The index can also be calculated based on any combination of data including high data point(s), low data point(s), average data point(s), derivatives of various orders, and other forms of direct or indirect data based on sEMG data.

The different data points can be weighted. For example, high data points, low data points, average data points, data points taken during a particular time period, data points taken from a particular muscle group, data points taken while the individual is performing a particular task, and/or data points taken based upon some other criteria can be assigned a weight, and the index can be calculated taking into consideration these different weights.

Additionally, the index serves as a snapshot of muscular health at a given point in time. Snapshots can be used to evaluate individuals and populations of individuals as a one-time evaluation of health, or pre- and post-treatment as discussed in further detail below. Snapshots may also serve to provide a statistical and meaningful basis for describing the efficacy of various treatment methods for repetitive strain injury and other disorders, such as those involving chronic pain, muscles, biological electrical activity or others.

Figure 4:
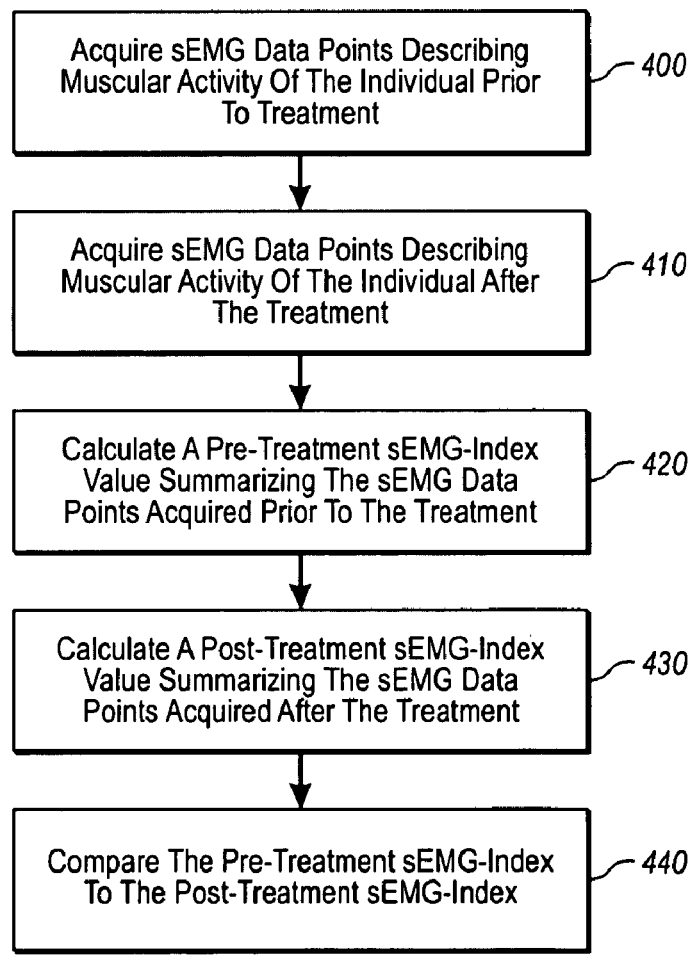
FIG. 4 illustrates a method for evaluating a change in muscle health due to treatment.

For example, a method for evaluating a change in muscular health of an individual before and after treatment is illustrated in FIG. 4. The method can include acquiring sEMG data points describing muscular activity of the individual prior to the treatment (400) and acquiring sEMG data points describing muscular activity of the individual after the treatment (410). A pre-treatment index is calculated from the sEMG data points describing muscular activity of the individual prior to the treatment (420). A post-treatment index is calculated from the sEMG data points describing muscular activity of the individual after the treatment (430). The pre-treatment index is compared to the post-treatment index (440) to evaluate the treatment. For example, the comparison can be used to evaluate whether the treatment resulted in an improvement in muscular health by decreasing muscle use during some standardized activity. The indices can be calculated according to any of the algorithms and processes set forth herein.

The method of FIG. 4 can be performed for multiple individuals. The pre-treatment index values calculated for the individuals can be averaged to produce a pre-treatment population index value. The post-treatment index values calculated for the multiple individuals can be averaged to produce a post-treatment population index value. Based on the pre-treatment and post-treatment population indices, the effectiveness of the treatment on the population can be evaluated.

Figure 5:
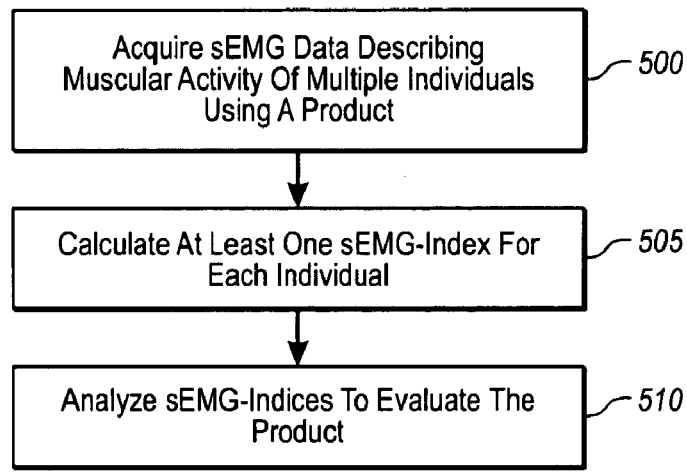
FIG. 5 illustrates a method for evaluating a product.

Similar to evaluating a treatment, the index can be used to evaluate a product. The product can be evaluated to determine if the product creates a risk to the health or determine its ergonomic effectiveness. For example, referring to FIG. 5, a method for evaluating a product is illustrated. The method includes acquiring sEMG data points describing muscular activity of multiple individuals using a product (500). The sEMG data points can be acquired while the individuals are using the product (for a fixed period of time, or for a fixed task, for example) to determine the muscular strain on the individuals while the individuals are using the product. The sEMG data points can also be acquired before the individuals use the product and after the individuals use the product to evaluate whether any damage or lasting muscular, neuromuscular, or musculoskeletal change has occurred as a result of the individuals' use of the product. Certain muscles may be targeted by the sEMG data points. For example, if the product being evaluated is a computer mouse, certain muscles within the arms of the individuals may be targeted or weighted more significantly so as to assess the risk of a repetitive strain injury.

At least one index is calculated for each individual (505) from the sEMG data points describing muscular activity of the individuals during, prior, and/or after use of the product. The indices are analyzed (510) to evaluate whether the product resulted in a risk to muscular health. The indices can be calculated according to any of the algorithms set forth herein. The method of FIG. 5 can also be performed for different products and the results compared to evaluate a relative risk between the different products.

The methods disclosed herein can be used to assess the muscular health of a population. For example, the muscular health of a group of individuals, such as the employees of a company or individuals in a locality, may be evaluated using index values calculated for each individual to determine an average muscular health of the population. The relative muscular health of the individuals may also be assessed to identify potential individuals at risk, and changes with regard to the at-risk individuals may be implemented to ensure that expenditures related to improving muscular health of the population are spent on individuals with whom the efforts will find the most overall benefit. Thus, a company, insurance company, regulatory body, or other entity interested in maintaining the health of a population can tailor efforts so as to increase the overall effectiveness of such efforts.

Figure 6:
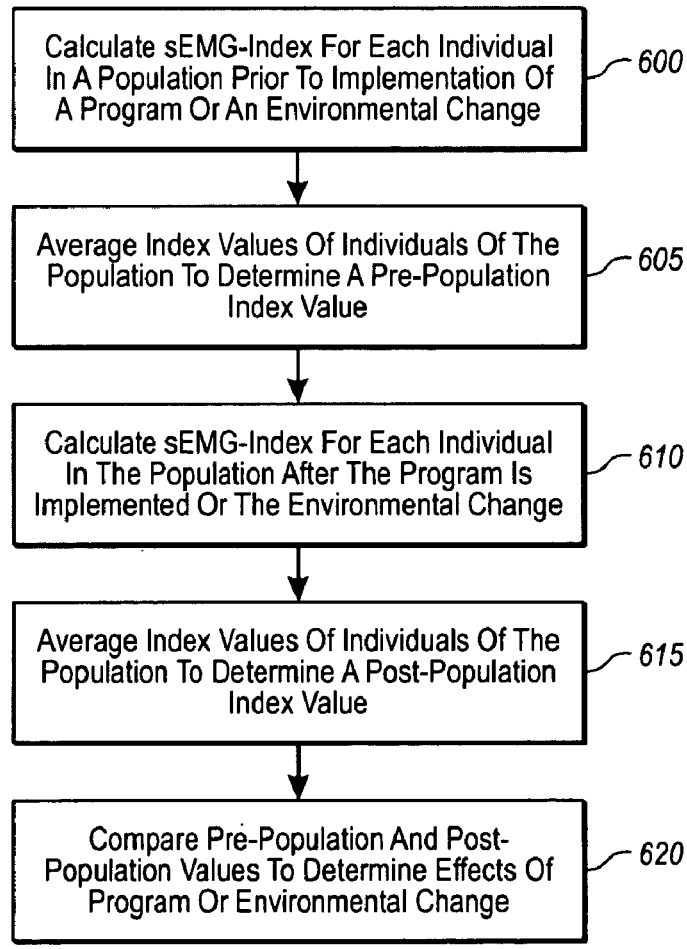
FIG. 6 illustrates a method for determining the effects of a program or environmental change.

The methods disclosed herein may also be used to assess a change in muscular health of a population. A change in muscular health of the population can be assessed, for example, by calculating index values for each individual in the population at two points in time (e.g., see FIG. 4). The two points in time may be prior to, and after, a treatment of the population or a change in an environmental condition for the population. For example, a company may want to implement a program or an environmental change for the company's employees. For example, the company may want to invest in an exercise program or purchase ergonomic equipment for its employees. The company may also want to be able to determine that the program or environmental change actually improved the muscular health of the company's employees. Therefore, referring to FIG. 6, the company performs one or more of the methods disclosed herein to calculate index values for the employees before the program, or environmental change was implemented (600). The company also performs one or more of the methods disclosed herein to calculate index values for the employees after the program or environmental change was implemented (610). The company compares the pre-program or pre-environmental change index values to post-program or post-environmental change index values to determine if the program or environmental change had the desired effects (620). Thus, the company would be able to evaluate whether the program or environmental changes justified their costs in improved muscular health of the population.

Figure 7:
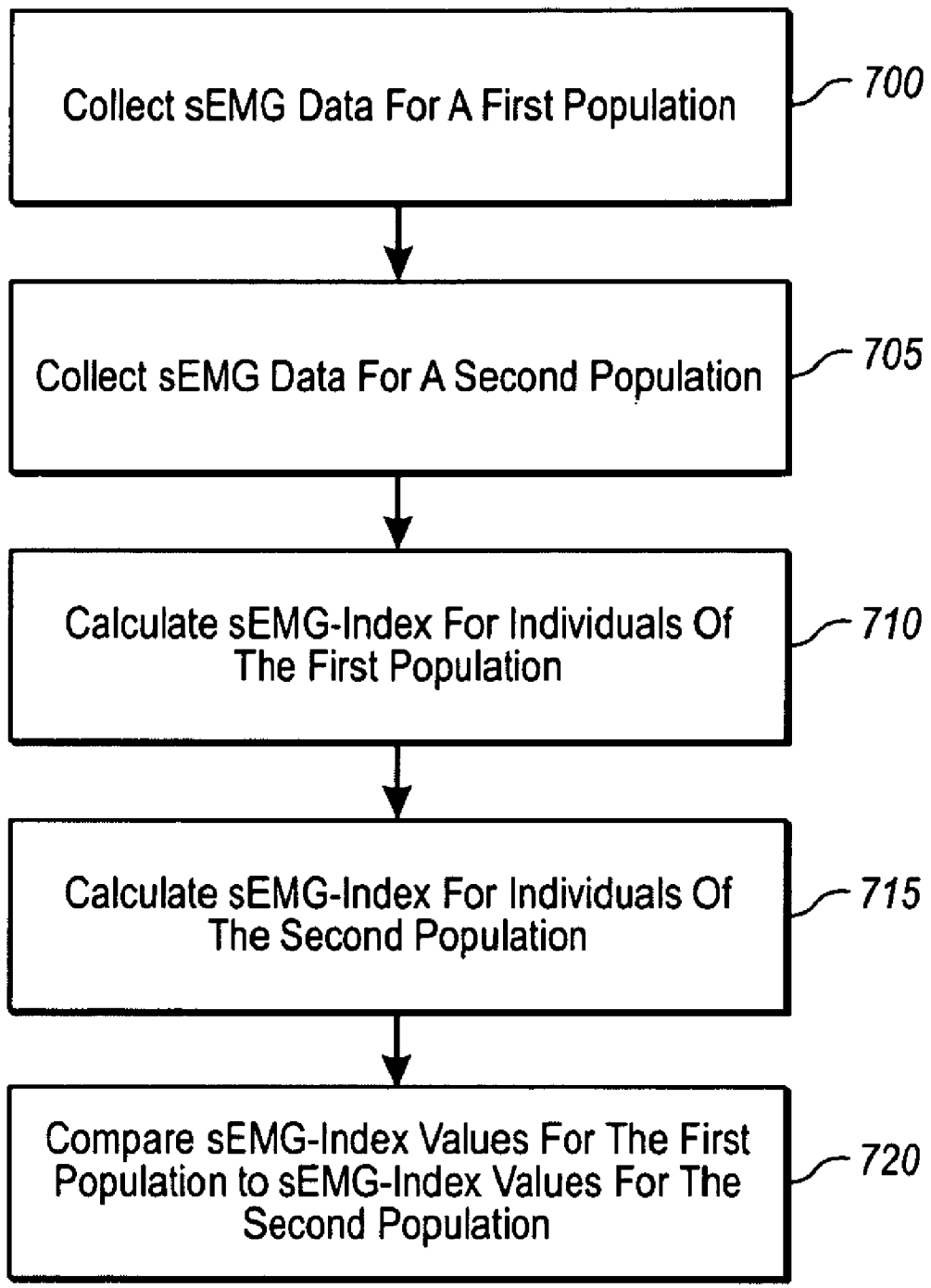
FIG. 7 illustrates a method for assessing the relative muscular health, or change in relative muscular health, between individuals or multiple populations.

Moreover, the methods disclosed herein can be used to assess the relative muscular health, or change in relative muscular health, between multiple populations. For example, referring to FIG. 7, sEMG data is collected for a first population (700). sEMG is also collected for a second population (705). Index values are calculated for the first population (710) using any of the methods disclosed herein. Index values are also calculated for the second population (715) according to any of the methods disclosed herein. The index values calculated for the first population are compared to the index values for the second population (720). The comparison between populations may be assessed to determine relative health risks between the populations. The relative risks may be used for insurance purposes, training effectiveness purposes, or to identify populations having a particular attribute or lifestyle that attributes to muscular unhealthiness or healthiness.

The relative muscular health of populations calculated by index values can be used to evaluate the effect of treatments, activity, and environmental conditions. For example, index values for each individual within two or more populations can be assessed prior to, and after, a treatment, activity, or change in environmental condition. Thus, the methods of FIGS. 3-7 may be performed at many points in time and the relative change in index can be compared over time. The change in index values can be compared to determine the effect of the treatment, activity, or change in environmental condition. As such, a more standardized analysis can be conducted over individuals and populations of individuals.

According to any of the embodiments disclosed herein, an index can be output to an electronic device. For example, an index can be output to an electronic device such as a display. The index can also be stored in memory, printed, or output in any other manner.

D. Cognitive Stress Measures

It is well-established that psychological stress or cognitive factors, even in the absence of physical demands, can increase muscle tension as reflected in sEMG index values. Psychological stressors which introduce physiological stress can be in various forms. For example, mental tasks, distractions, and unpleasant environments can often introduce physiological stress which can be evaluated by the sEMG index values disclosed herein.

The psychological stressors can be in the form of cognitive tasks. These cognitive tasks can include mental recognition tasks, mathematical tasks, and combinations of mental and motor skill tasks where distracters can be introduced to increase the level of stress experienced by a subject during completion of the cognitive and physical tasks. Any number and combination of test stations introducing psychological stressors can be implemented and any combination of cognitive and/or physical tasks may be used. However, where the effects of a particular real-life environment are of interest, the psychological stressors used can be selected to more closely replicate the stressful environment encountered in real-life.

Additional indicators that may be used in the present invention to evaluate stress response levels include systolic and diastolic blood pressure, heart rate, urinary epinephrine and norepinephrine, and salivary cortisol. Other aspects of the subject's response to psychological tasks, such as response time and response accuracy, can also be assessed separately or in combination with the index values calculated form the sEMG data obtained while the subject is performing cognitive tasks.

2. The Test Circuit

Embodiments of the present invention include a test circuit for measuring physiological stress responses. A test circuit includes multiple test stations that are each designed to simulate a particular task that is associated with increased stress levels. Generally, where a test circuit is created to evaluate the risk of stress-related injuries associated with a particular activity, the stations of the test circuit can each be configured to reproduce (or emphasize) the types of physical and/or mental stress and levels of stress involved in performing that particular activity.

A. Test Circuit Equipment

Figure 8:
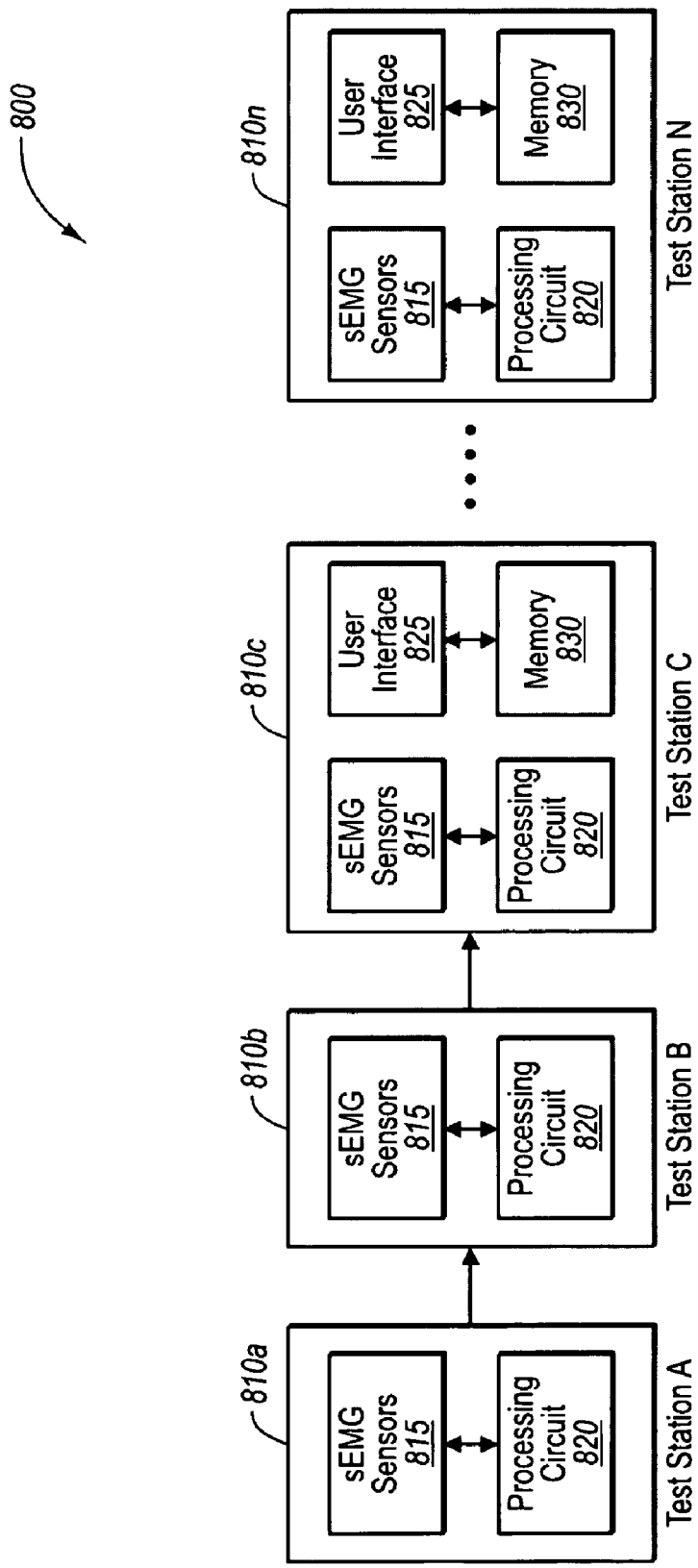
FIG. 8 illustrates an example test circuit that may be used to evaluate physiological and psychological stress responses.

FIG. 8 illustrates an example of a test circuit 800 that may be used to implement features of the present invention. A test circuit 800 can include a plurality of test stations 810, which may include physiological test stations, psychological test stations, and/or a combination thereof. In this example, Test Station A 810a and Test Station B 810b can each represent a physiological only test station, Test Station C 810c can represent psychological only test stations, and Test Station N 810n can represent a combination physical and psychological test station. Any number and combination of different tests stations, and physical and psychological stressors introduced thereby, can be implemented.

Figure 2:
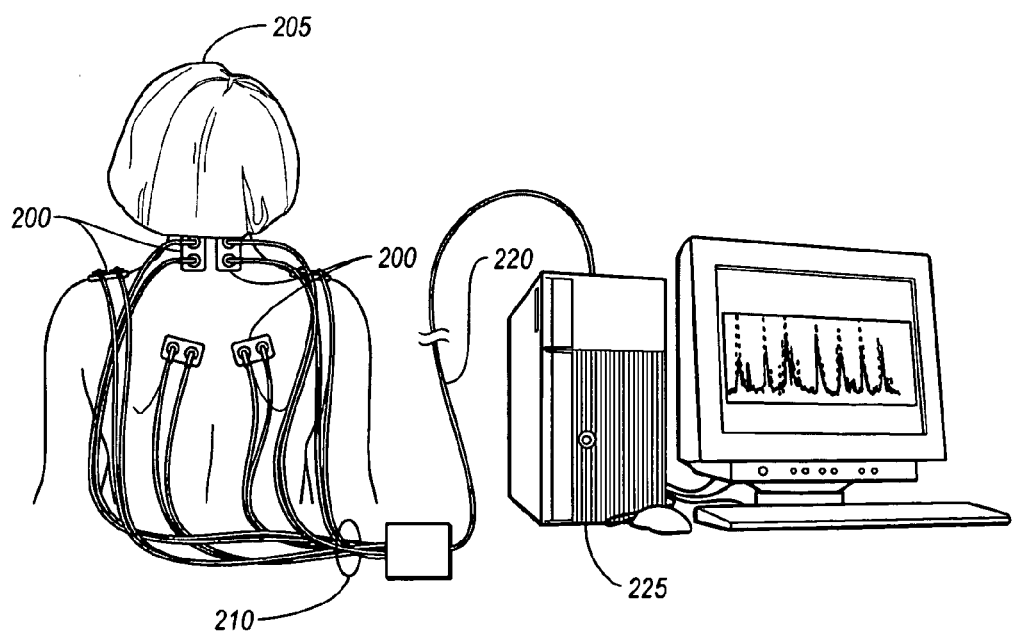
FIG. 2 illustrates a system for collecting sEMG data.

As shown in Test Station A 810a and Test Station B 810b, each physiological test station includes sEMG sensors 815 for collecting sEMG data describing muscular activity of the subject while the subject performs the task associated with that particular station. An example illustration of sEMG sensors that may be included in a physiological test station is illustrated in FIG. 2 discussed above. Each physiological test station 810a and 810b also includes a processing circuit 820 that is communicably coupled to the sEMG sensors 815 for calculating an index value based on the sEMG data collected by the sEMG sensors 815.

Psychological Test Station C 810c includes a user interface 825 for guiding the subject through the execution of the one or more cognitive tasks. Psychological Test Station C 810c can also have memory 830 communicably coupled to the user interface 825 for storing the relevant task and recording the subject's responses to the one or more cognitive tasks. Test Station C 810c also includes sEMG sensors 815 for collecting sEMG data describing muscular activity of the subject while the subject completes the one or more cognitive tasks. The psychological Test Station C 810c also includes a processing circuit 820 that is coupled to the sEMG sensors 815 for calculating an index valve based on the sEMG data.

Additionally, the test circuit 800 may include a Test Station N 810n that includes the components of both a physiological and psychological test station as previously discussed regarding Test Stations 810a, b, and c. Further, depending on the particular task required, a test station also includes the components necessary to perform the required task, as will be described in detail hereinafter.

B. Test Station Tasks

The stations of a test circuit and the required tasks therein are each configured to reproduce the types of stress and levels of stress involved in performing a predetermined physical and/or psychological activity. Since the stress associated with the predetermined activity is reproduced in the test circuit environment, the physical and neuromuscular effects of that stress can be measured and quantified. Thus, in order to obtain the most accurate and reliable data, the tasks of a test station should properly reproduce the stress-inducing tasks associated with the predetermined activity.

In one embodiment, a test station may include a driving simulation task. The driving simulation task may require the subject to use a full-motion driving simulator to complete a custom driving course. The simulated driving course may include several physical and psychological stressors commonly associated with driving including slippery roads, reckless drivers, police cars, loud noises, etc.

The driving simulation can be included in the first test station for at least two reasons. First, in order to accurately replicate events and activities associated with a particular environment, the chronological order of those events and activities can advantageously be taken into consideration. Since many people drive to work and perform similar recreational activities, putting a driving simulation task in the test circuit before other tasks serves to replicate the subject's actual stress levels on a typical day when starting tasks after a commute. In other words, by replicating a typical commute, the subject's stress levels when beginning other tasks are more consistent with, and indicative of, real-life.

The second reason that the driving simulation can be included in the first test station involves the normalization of the test group. In a given test group, some subjects may commute for an hour or more to get to the testing location and may therefore have a relatively high stress level when they arrive. Others in the test group may not commute at all and may therefore have a relatively low stress level. Putting the driving simulation first serves to normalize the stress values of the test group to the same level at the beginning of the circuit.

A next station may include one or more tasks in which gross motor skills are utilized. Gross motor skills involve large motor movements and generally relate to the type of stress-related injuries caused by lifting heavy objects or poor body mechanics. Measuring the risk of stress-related injury involved in gross motor movement is relevant for occupations that require lifting heavy objects, construction work, and the like. To replicate the stress caused by these activities, a subject may be required to perform specific tasks with a number of heavy objects, such as a series of medicine balls or similarly weighted objects. Typical tasks may include moving a medicine ball from one box to another, moving a medicine ball from the floor to a shelf, throwing a medicine ball at a trampoline which is mounted at a 45 degree angle and catching the medicine ball, and/or other physical gross motor tasks. The different tasks and weights used in the gross motor test station can be configured to replicate the movement required in an actual work environment.

Yet another station may include a task that requires the subject to multitask with a keyboard and mouse while being exposed to additional stress. Prolonged keyboard and mouse use can lead to repetitive strain injuries and cumulative stress disorders such as carpal tunnel syndrome. This task can include a keyboard component and a mouse component and may be performed under conditions typically associated with a work environment. In one embodiment, a subject is required to perform a keyboard component that requires the subject to stay focused and pay close attention to detail presented to the subject while being exposed to several distractions including visual and audio stimuli. For instance, the subject may be required to type a complex entry from a source window to a destination window. Visual distracters, such as changing fonts, changing colors, and movement of the text across the screen can also be introduced. Audible distracters can be included. For example, audible music, distracting noise, and/or recorded speech can be played on either side of the screen. Similarly, a subject may be required to perform different mouse tasks (right-click, left-click, double-click, etc.) under the same distracting conditions. By introducing several distractions while the subject performs the tasks, this test station can replicate the psychological and physiological stresses often associated with busy work environments.

To evaluate the effect of cognitive stress, a test circuit station may include a task involving a test similar to what is referred to as a "Stroop" test. In addition to being a psychological stressor, a Stroop test is also used as a neuropsychological tool for evaluation of some cognitive functions such as selective attention, cognitive elasticity, and general dysinhibition. In the Stroop test's original version defined by J. Ridley Stroop in 1935, subjects were required to read the written meaning of words with differing colored fonts and to verbally identify the color of each printed color name. When a word such as blue, green, red, etc. is printed in a color differing from the color expressed by the word's semantic meaning (i.e. the word "red" printed in blue ink), a delay may occur in the processing of the word's color, leading to slower test reaction times and an increase in mistakes and stress caused thereby. Since the inception of the Stroop test, several modified test versions have been developed. In order to increase the stress associated with the Stroop test, additional stressors may be introduced during the test such as informing a subject that time is running out or informing the subject that the test is being recorded and/or scored. In one embodiment, a Stroop test is administered at a test circuit via a user interface, such as a computer interface. During this Stroop test sEMG data is acquired and analyzed.

Another task that may be included in a test circuit to evaluate the physiological effect of cognitive stress is a mathematical processing task in which the subject is asked to add, subtract, divide or multiply numbers. In one embodiment, a subject is required to perform serial subtraction, such as repeatedly subtracting a random two-digit number from a four-digit number, or counting backwards from a four-digit number by increments of a two digit number (i.e., count backwards from 4567 by 17's). In this test, the subject is not allowed to use a pencil and paper, and must say the answers out loud. Since the task requires executive control, memory and interaction with the verbal system, several elements of the effects of the physiological stress may be evaluated. Similarly to the Stroop test, additional stressors may be introduced as the mathematical processing test is being administered. A subject may be informed that the test is being video taped for further observation. When a subject gives the wrong answer, the subject may be told to start over at the last correct number. As an additional stressor, a subject may also be told to go faster because time is running out.

In each case, sEMG data is acquired while the subject is completing the required task at each test station. From the sEMG data, one or more index values can be calculated. Based on these one or more index values the physiological effect on the subject can be ascertained and evaluated. While not necessary to the teachings disclosed herein, the subject's responses to the cognitive tests, such as accuracy and speed, can also be collected and assessed.

The muscular activity monitored by the sEMG data can be voluntary or involuntary muscular activity. Moreover, the differences in the levels of physiological effects between voluntary and involuntary muscular activity can also be evaluated. For example, the muscular activity of the subject during voluntary movement of an object or voluntary movement of a computer mouse may be different than the involuntary muscular tension introduced by psychological stressors. Therefore the physiological effects of voluntary and/or involuntary movements can be assessed and evaluated to determine the physiological effects of the various tasks on a particular subject.

Any task in which an evaluation of the associated level of stress is desired may be included in a test station. Depending on the environment being studied, cognitive effects, physiological effects, or a combination thereof may be evaluated.

3. Risk of Stress-Related Injury

The sEMG index values can be used to evaluate the effects of stress while performing a particular activity. By exploring physiological responses to different stressors, a better understanding of stress-related injuries may be achieved.

Figure 9:
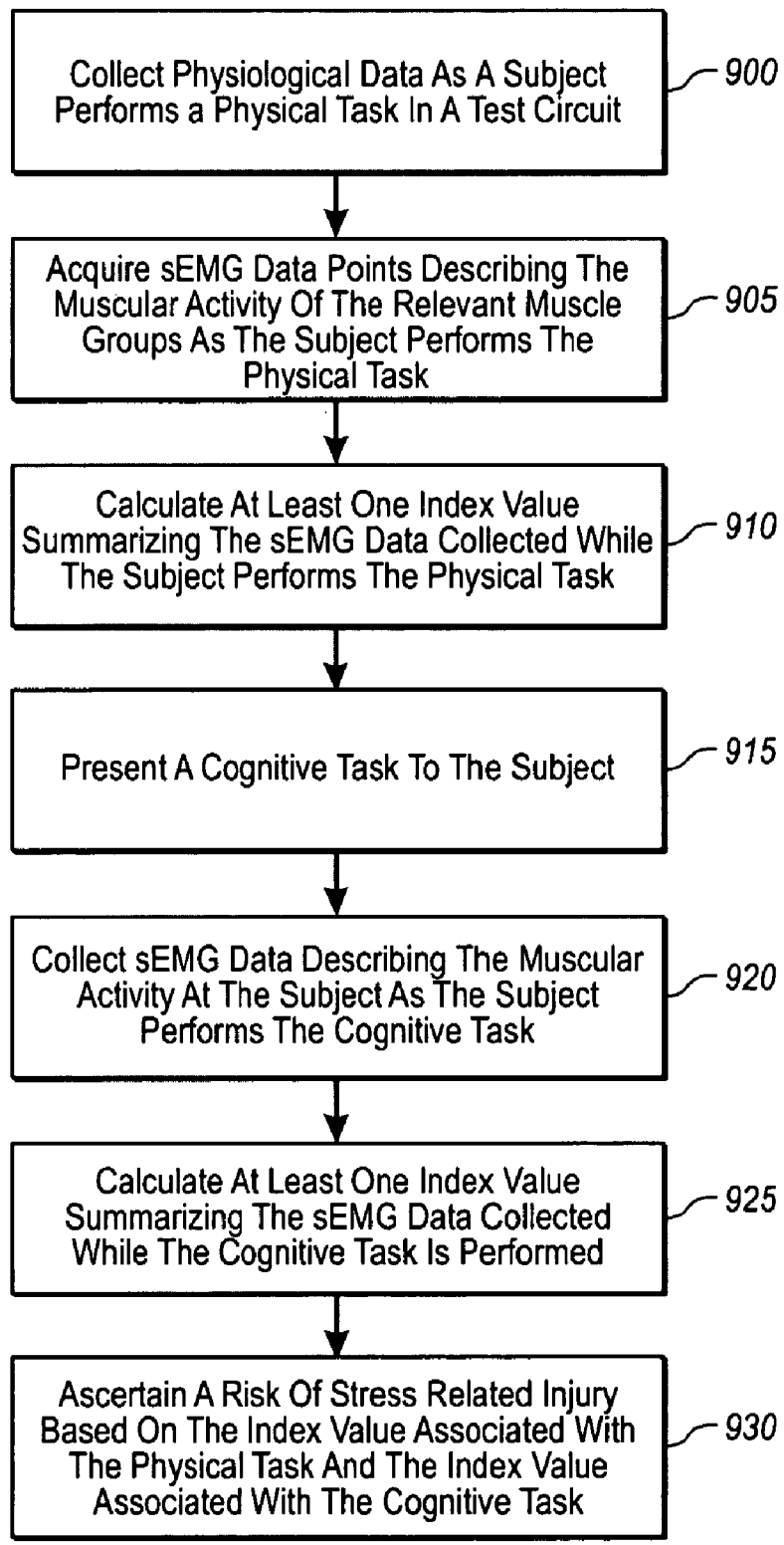
FIG. 9 illustrates a method for determining the risk of stress-related injury associated with a predetermined activity.

Referring to FIG. 9, a method for determining the risk of stress-related injury associated with a predetermined activity is illustrated. Physiological data is collected as a subject performs a physical task in a test circuit (900). The test circuit can be configured to include one or more physical tasks that are relevant to the predetermined activity that is being evaluated. As the subject performs the physical task, sEMG data points are acquired describing the muscular activity of a relevant muscle group (905). The muscle group that is monitored during the performance of the task can be based on the particular activity being performed. The number of tasks performed in a test circuit can be unlimited as any number of tasks may be included in the methods described herein. For each of the physical tasks performed, at least one index value is calculated summarizing the sEMG data associated with that task (910). Any method of calculating the index described herein may be used to summarize the sEMG data (for example, see Section 1A). One or more cognitive tasks are presented to the subject (915). sEMG data is collected as the subject performs the cognitive task in the test circuit (920). At least one index valve is calculated summarizing the sEMG data collected while the cognitive task is performed (925). The one or more cognitive tasks may include a Stroop test and/or a mathematical processing task as described herein, for example. Results can also be collected and can include the subject's responses to the cognitive tasks. Responses may be recorded by a task administrator or with audio equipment. Based on the index values calculated, a risk of stress related injury is ascertained (930).

Figure 10:
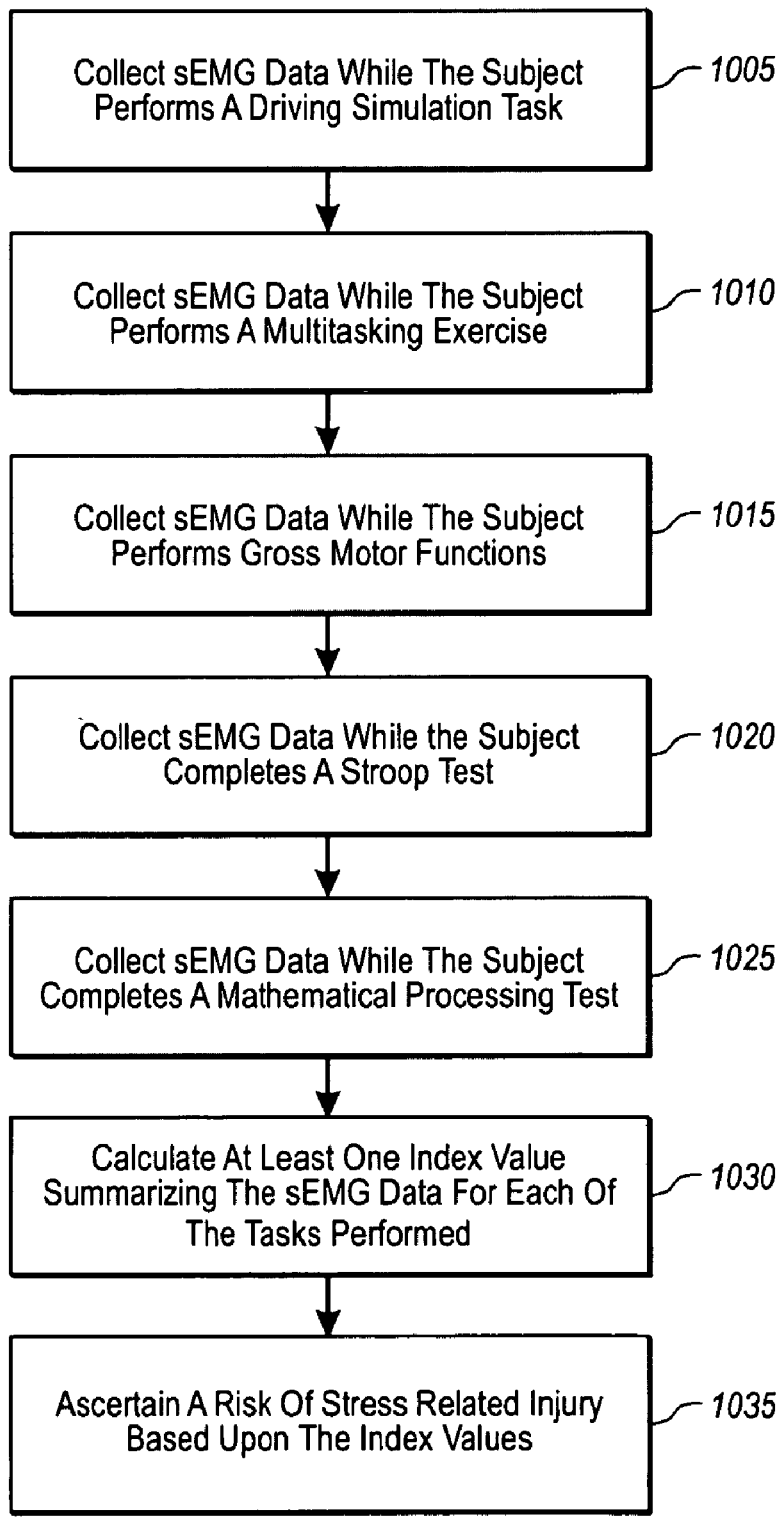
FIG. 10 illustrates a method for determining the risk of stress-related injury associated with an occupational setting.

As discussed herein, tasks in a particular test circuit can be chosen and configured to replicate tasks commonly associated with a predetermined activity being evaluated for stress-related injury. FIG. 10 illustrates an example of a method for evaluating the risk of stress-related injury associated with an occupational setting sEMG data is collected while a subject performs a driving simulation task (1005). The driving simulation task can be configured to simulate a typical commute to the workplace that the subject may experience and may include slippery road conditions, reckless drivers, police cars and the like.

Next, the subject moves to the next station in the circuit where sEMG data is received as the subject performs a multitasking exercise (1010). The multitasking exercise can include performing tasks on a computer with a keyboard and mouse in a manner typically associated with administrative or office work. Additional stressors that may be added to the multitasking exercise include changing the colors of the display and playing audio that replicates the noise that may be experienced in a workplace setting.

In the next test station, sEMG data is collected while the subject performs gross motor functions (1015). Gross motor functions may include lifting and moving heavy objects in a manner typically associated with an occupational setting such as an assembly line in a manufacturing facility or a construction site. For each of the physiological tasks performed, at least one index value is calculated summarizing the sEMG data (1020).

At a next test station, sEMG data is collected as the subject completes a Stroop test (1025). The subject's response times to the Stroop test may also be recorded.

At another test station, sEMG data is collected as a subject responds to a mathematical processing test (1030). Additional stressors that may be introduced during cognitive tasks can include rushing the subject through the task and noticeably recording the subject's performance. At least one index value is calculated from the sEMG data collected for each task performed (1030). For example, at least one index value can be calculated from the sEMG data gathered during each task. These multiple index values can be combined in to a single index value and analyzed as a whole, or the multiple index values can be left separate for analysis. The different index values can also be weighted where one task is determined to be more important than another task. Thus, a weight can be assigned to the sEMG index value associated with each task and the weighted sEMG values can be subsequently combined to arrive at a single individual being tested. Finally, the risk of stress-related injury associated with an occupational setting is ascertained based on the index values (1035). For example, the single (or multiple) index values calculated for a particular individual can be compared to the index values of a population within which the individual belongs. This population can be coworkers, others of similar age, occupation, and/or a population exposed to a similar environment or product. Therefore, individuals who have a relatively high likelihood of a stress-related injury compared with others of the same population can be identified based on the sEMG data acquired during the test circuit.

Embodiments within the scope of embodiments illustrated herein can also include computer-readable media for carrying or having computer-executable instructions or data structures stored thereon for performing the methods disclosed herein. For example, these computer-executable instructions can be configured to cause a computer or other device to gather sEMG data and/or to calculate index values. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media. Computer-executable instructions comprise, for example, instructions and data which cause a general purpose computer, special purpose computer, or special purpose processing device to perform a certain function or group of functions such as those disclosed herein.

Figure 11:
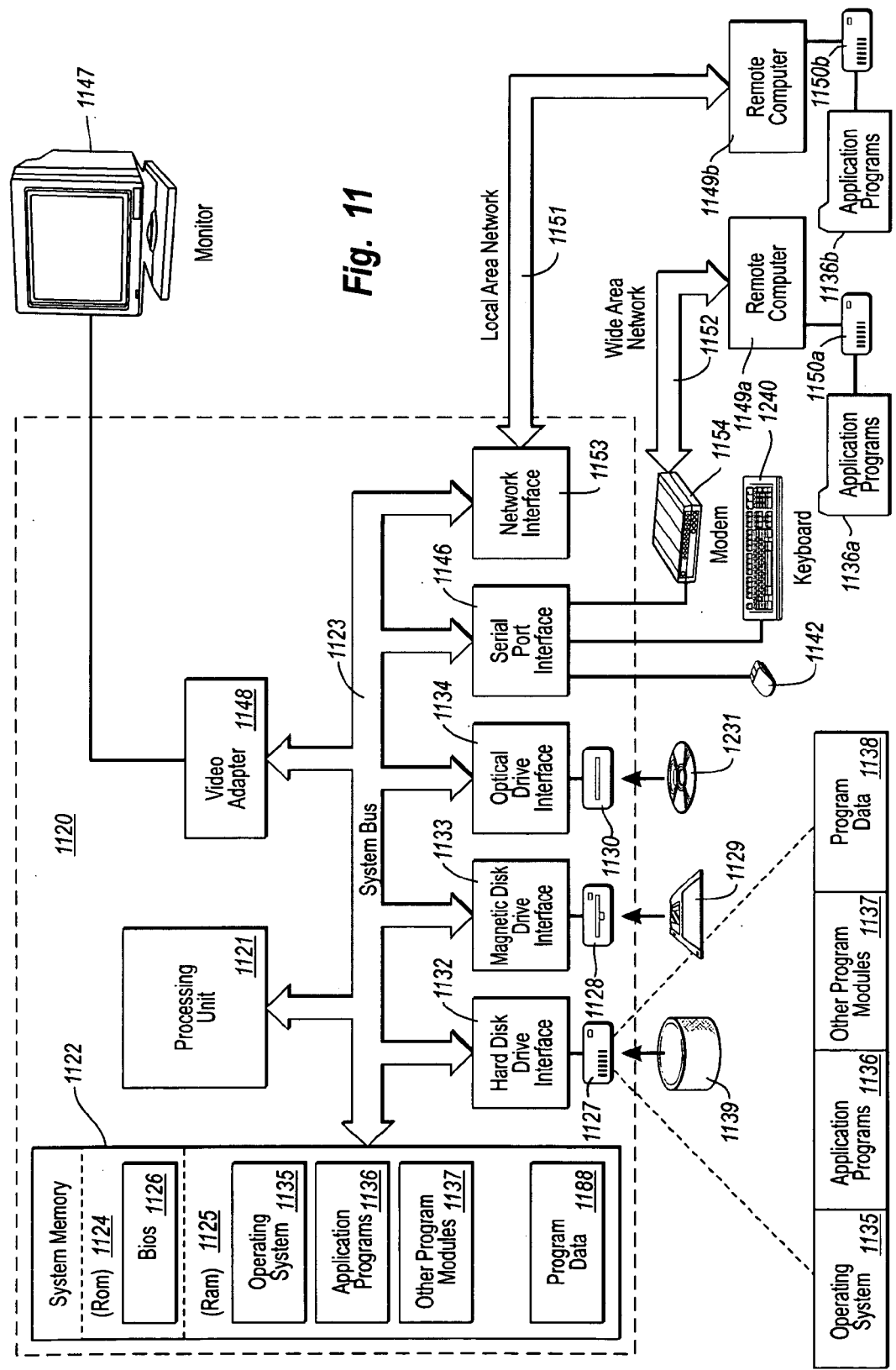
FIG. 11 provides a brief, general description of a suitable computing environment in which several embodiments may be implemented.

FIG. 11 and the following discussion are intended to provide a brief, general description of a suitable computing environment in which several embodiments may be implemented. Although not required, several embodiments will be described in the general context of computer-executable instructions, such as program modules, being executed by computers in network environments. Generally, program modules include routines, programs, objects, components, data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Those skilled in the art will appreciate that the embodiments illustrated herein may be practiced in network computing environments with many types of computer system configurations, including personal computers, hand-held devices, multi-processor systems, microprocessor-based or programmable consumer electronics, network PCs, minicomputers, mainframe computers, and the like. Several embodiments may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

With reference to FIG. 11, an example of a system for implementing several embodiments includes a general purpose computing device in the form of a conventional computer 1120, including a processing unit 1121, a system memory 1122, and a system bus 1123 that couples various system components including the system memory 1122 to the processing unit 1121. The system bus 1123 may be any of several types of bus structures including a memory bus or memory controller, a peripheral bus, and a local bus using any of a variety of bus architectures. The system memory includes read-only memory (ROM) 1124 and random access memory (RAM) 1125. A basic input/output system (BIOS) 1126, containing the basic routines that help transfer information between elements within the computer 1120, such as during start-up, may be stored in ROM 1124.

The computer 1120 may also include a magnetic hard disk drive 1127 for reading from and writing to a magnetic hard disk 1139, a magnetic disk drive 1128 for reading from or writing to a removable magnetic disk 1129, and an optical disk drive 830 for reading from or writing to removable optical disk 1131 such as a CD ROM or other optical media. The magnetic hard disk drive 1127, magnetic disk drive 1128, and optical disk drive 1130 are connected to the system bus 1123 by a hard disk drive interface 1132, a magnetic disk drive-interface 1133, and an optical drive interface 1134, respectively. The drives and their associated computer-readable media provide nonvolatile storage of computer-executable instructions, data structures, program modules and other data for the computer 1120. Although the exemplary environment described herein employs a magnetic hard disk 1139, a removable magnetic disk 1129 and a removable optical disk 1131, other types of computer readable media for storing data can be used, including magnetic cassettes, flash memory cards, digital versatile disks, Bernoulli cartridges, RAMs, ROMs, and the like.

Program code means comprising one or more program modules may be stored on the hard disk 1139, magnetic disk 1129, optical disk 1131, ROM 1124 or RAM 1125, including an operating system 1135, one or more application programs 1136, other program modules 1137, and program data 1138. A user may enter commands and information into the computer 1120 through keyboard 1140, pointing device 1142, or other input devices (not shown), such as a microphone, joy stick, game pad, satellite dish, scanner, or the like. These and other input devices are often connected to the processing unit 1121 through a serial port interface 1146 coupled to system bus 1123. Alternatively, the input devices may be connected by other interfaces, such as a parallel port, a game port or a universal serial bus (USB). A monitor 1147 or another display device is also connected to system bus 1123 via an interface, such as video adapter 848. In addition to the monitor, personal computers typically include other peripheral output devices (not shown), such as speakers and printers.

The computer 1120 may operate in a networked environment using logical connections to one or more remote computers, such as remote computers 1149*a* and 1149*b*. Remote computers 1149*a* and 1149*b* may each be another personal computer, a server, a router, a network PC, a peer device or other common network node, and typically include many or all of the elements described above relative to the computer 1120.

When used in a LAN networking environment, the computer 1120 is connected to the local network 1151 through a network interface or adapter 1153. When used in a WAN networking environment, the computer 1120 may include a modem 1154, a wireless link, or other means for establishing communications over the wide area network 1152, such as the Internet. The modem 1154, which may be internal or external, is connected to the system bus 1123 via the serial port interface 1146. In a networked environment, program modules depicted relative to the computer 1120, or portions thereof, may be stored in the remote memory storage device. It will be appreciated that the network connections shown are examples and other means of establishing communications over wide area network 1152 for calculating the indices and performing the methods disclosed herein.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. Detailed descriptions of apparatus and processing techniques known in the field of the invention to one of ordinary skill in the art have been excluded.

The principles of the embodiments described herein describe the structure and operation of several examples used to illustrate the present invention. It should be understood that the drawings are diagrammatic and schematic representations of such example embodiments and, accordingly, are not limiting of the scope of the present invention, nor are the drawings necessarily drawn to scale. Well-known devices and processes have been excluded so as not to obscure the discussion in details that would be known to one of ordinary skill in the art.

I claim:

1. A method for assessing the physiological effect of physiological and psychological stressors on a subject, the method comprising:

presenting the subject with a first physiological stressor;

receiving surface electromyography (sEMG) data points describing muscular activity of the subject while the subject is experiencing the physiological stressor;

presenting the subject with a first psychological stressor;

receiving sEMG data points describing muscular activity of the subject while the subject is experiencing the psychological stressor;

calculating a first index value summarizing at least a portion of the sEMG data points received while the subject is presented with the psychological stressor; and calculating a second index value summarizing at least a portion of the sEMG data points received while the subject is presented with the physiological stressor, wherein the act of analyzing the sEMG data points includes analyzing the first and second index values.

2. A method according to claim 1, further comprising ascertaining a risk of the subject developing a stress-related injury based at least in part on the first and second index values.

3. A method according to claim 1, wherein the first physiological stressor includes one or more predetermined physical tasks.

4. A method according to claim 3, wherein the one or more physical tasks include a driving simulation task that requires the subject to perform a simulated driving course on a driving simulator, wherein the simulated driving course further includes a second psychological stressor presented to the subject while the subject is performing the one or more physical tasks.

5. A method according to claim 4, wherein the second psychological stressor includes at least one of a slippery road condition, a police car, a reckless driver, and a loud noise in the simulated driving course.

6. A method according to claim 3, wherein the one or more physical tasks include a gross motor task.

7. A method according to claim 6, wherein the gross motor task requires the subject to perform at least one of lifting an object, moving an object, catching an object, and throwing an object.

8. A method according to claim 3, wherein the one or more physical tasks includes a multitasking task that requires the subject to perform physical exercises utilizing a keyboard, a mouse, a touchpad, and a microphone.

9. A method according to claim 8, further comprising a second psychological stressor that includes at least one of distracting noise, changing fonts, moving virtual windows, and changing display colors that is presented to the subject simultaneously with the one or more physical tasks.

10. A method according to claim 1, wherein the first psychological stressor includes one or more cognitive tasks.

11. A method according to claim 10, wherein the one or more cognitive tasks include at least one of:
requiring the subject to read and recite the name of a word, wherein the semantic meaning of the presented word is a color other than the color of the presented word; and
requiring the subject to perceive and recite the color of the presented word, wherein the semantic meaning of the presented word is a color other than the color of the presented word.

12. A method according to claim 10, wherein the one or more cognitive tasks includes a mathematical processing test presented to the subject, wherein the mathematical processing test requires the subject to perform a series of at least one of addition, subtraction, multiplication, and division exercises aloud.

13. A method according to claim 1, wherein calculating the first and second index values summarizing the sEMG data points includes at least one of:
calculating the index value based at least in part on an area under a curve, the curve approximating at least a portion of the sEMG data points;
calculating the index value based at least in part on an area over the curve;
calculating the index value based at least in part on an average of multiple high data points or an average of multiple low data points;
calculating the index value based at least in part on a combination of a high data point, a low data point, and an average of multiple data points;
calculating the index value based on a derivative of one or more orders; and
calculating the index value based at least in part on a combination of a high data point (H), a low data point (L), and an average data point (A) according to the following equation:

$$DH+CL+BA=E,$$

where D, C, and B describe weights assigned to the high data point, low data point, and average data point.

14. A method according to claim 13, wherein the area under the curve or the area over the curve is calculated by taking an integral of at least a portion of an sEMG graph representing the sEMG data points.

15. A method according to claim 13, wherein the area under the curve or the area over the curve is calculated by taking a weighted integral or double integral of at least a portion of an sEMG graph representing the sEMG data points.

16. A non-transitory computer readable medium having computer executable instructions stored on the computer readable medium, the executable instructions being configured to cause a computer to perform the acts of claim 1 when executed by the computer.

* * * * *

UNITED STATES PATENT AND TRADEMARK OFFICE
CERTIFICATE OF CORRECTION

| | | |
|---|---|---|
| PATENT NO. | : 8,126,542 B2 | Page 1 of 1 |
| APPLICATION NO. | : 12/332111 | |
| DATED | : February 28, 2012 | |
| INVENTOR(S) | : Grey | |

It is certified that error appears in the above-identified patent and that said Letters Patent is hereby corrected as shown below:

On the Title Page, in Field (74), under "Attorney, Agent or Firm", in Column 2, Line 1, delete "Machoff Golmore & Israelsen" and insert -- Maschoff Gilmore & Israelsen --, therefor.

Signed and Sealed this
Twenty-fourth Day of July, 2012

David J. Kappos
*Director of the United States Patent and Trademark Office*